US00PP08255P

United States Patent [19]

Jackson et al.

[11] Patent Number: Plant 8,255

[45] Date of Patent: Jun. 15, 1993

[54] GRANSUN NECTARINE TREE

[75] Inventors: James L. Jackson; Lance Jackson, both of Kingsburg, Calif.

[73] Assignee: Kings Gate Ranch, Inc., Kingsburg, Calif.

[21] Appl. No.: 709,696

[22] Filed: Jun. 3, 1991

[51] Int. Cl.[5] ..... A01H 5/00

[52] U.S. Cl. ..... Plt./41.1

[58] Field of Search ..... Plt./41, 41.1

[56] References Cited

U.S. PATENT DOCUMENTS

P.P. 2,794 2/1968 Anderson ..... Plt. 41

P.P. 5,241 6/1984 Apkarian ..... Plt. 41

*Primary Examiner*—James R. Feyrer

*Attorney, Agent, or Firm*—Worrel & Worrel

[57] ABSTRACT

A new and distinct variety of nectarine tree which produces fruit which is mature approximately May 15 through May 31 in the San Joaquin Valley of central California and which further produces a large round shaped fruit which is semi-clingstone by nature and which further exhibits a bright red coloration and a light yellow flesh.

1 Drawing Sheet

BACKGROUND OF THE NEW VARIETY

The present invention relates to a new and distinct variety of nectarine tree which will hereinafter be denominated varietally as the "Gransun" nectarine tree and, more particularly, to a nectarine tree which produces fruit which are mature for harvesting and shipment approximately May 15 through May 31 in the San Joaquin Valley of central California; which is further distinguished by producing round to somewhat oblong, semi-clingstone fruit having bright red skin coloration and flesh having a distinct aroma; and which has noteworthy shipping and handling characteristics.

The development of new commercial varieties of nectarine trees is less prolific than is the case with other fruit bearing trees. For example, existing varieties of peach trees number in the many hundreds while the number of existing nectarine tree varieties is significantly smaller. In developing markets for fresh fruit, those broad classes of varieties which are available substantially unabated throughout a long harvest season are generally better received in the marketplace than are those where no such dominance exists. The buying public is, in general, not sufficiently astute to watch for varieties which are rarely available and thereby are not trained to think of buying nectarines as opposed, for example, to peaches. Thus, the consumer may buy the varieties of peaches which are available even during those periods during which nectarines are available.

Accordingly, the discovery of a new variety of nectarine tree having commercial potential is a significant event in the development of commercial fruit varieties. This is particularly the case where the new variety of nectarine tree has the attributes of the present variety. Large size, attractive coloration, juicy flesh with a pleasing aroma and with good storage and shipping quality all contribute to the potential commercial appeal of the "Gransun" nectarine tree.

ORIGIN AND ASEXUAL REPRODUCTION OF THE NEW VARIETY

The present variety of nectarine tree hereof was discovered by the inventors in 1988 in their orchard which is located at Kingsburg in the central San Joaquin Valley of California. The new variety was discovered among "May Grand" nectarine trees and is a sport of the "May Grand" nectarine tree.

The sport of the new variety was asexually reproduced at the inventors' direction in 1990 by grafting scions of the sport of the subject invention onto rootstock of the "Primecrest" peach tree. The asexually reproduced tree of the subject invention first bore fruit in 1990 and the inventors observed in 1990 and 1991 that the fruit was in all respects identical to the parent.

SUMMARY OF THE NEW VARIETY

The "Gransun" nectarine tree is characterized as to novelty by producing a semi-clingstone fruit which is large for early season nectarines, round and bright red in color. The fruit produced by the nectarine tree matures for harvest approximately May 15 through May 31 or about twelve to fourteen days before the fruit of the "May Grand" nectarine tree, in the San Joaquin Valley of central California. The fruit is juicy and has a distinct aroma with a pleasing flavor.

BRIEF DESCRIPTION OF THE DRAWING

The accompanying drawing is a color photograph showing representative foliage including leaves displaying both the dorsal and ventral sides thereof;

a first nectarine shown in side elevation;

a second nectarine shown in side elevation and oriented to expose the suture thereof;

a third nectarine disposed in bottom plan view;

a fourth nectarine disposed in top plan view;

a fifth nectarine sectioned to expose the flesh thereof; and a pit, all of the new variety.

DETAILED DESCRIPTION

Referring more specifically to the pomological details of this new and distinct variety of nectarine tree, the following has been observed under the ecological conditions prevailing at the orchard which is located in Kingsburg, Calif. All major color code designations are by reference to the *Dictionary of Color*, by Maerz and Paul, Second Edition, published in 1950. On occasion, common designations as to coloration are employed.

TREE

Generally:
- *Size.*—Medium.
- Figure.—Spreading.
- Vigor.—Medium to high.
- *Productivity.*—Productive.
- *Regularity of bearing.*—Regular.

Trunk:
- *Surface texture.*—Smooth.
- *Surface characteristics.*—Medium.
- *Color.*—Lt. brown-silver.
- *Lenticels.—numbers.*—Numerous.
- *Diameter in relation to length.*—Medium.

Branches:
- *Size.*—Medium.
- *Surface texture.*—Smooth.
- *Surface character.*—Medium.
- *Color.*—Medium to dark reddish brown. Page 35, Plate 6, E-7.
- *Lenticels—numbers.*—Numerous.
- *Lenticels—size.*—2 mm (0.078 inches) by 6 mm (0.0236 inches).

LEAVES

Size:
- *Generally.*—Large.
- *Average length.*—150 mm (5.905 inches) to 160 mm (6.29 9inches).
- *Average width.*—38 mm (1.496 inches) to 40 mm (1.574 inches).

Color:
- Upwardly disposed surface.—Medium to dark green. Page 65, Plate 21, H-6.
- *Downwardly disposed surface.*—Light green. Page 63, Plate 20, E-7.

Marginal form: Finely serrate.

Shape: Lanceolate.

Petiole:
- *Length.*—10 mm (0.393 inches).
- *Thickness.*—2 mm (0.078 inches).

Stem glands:
- *Number.*—Two.
- *Form.*—Normal.
- *Position.*—Opposite.
- *Type.*—Reniform.
- *Color.*—Green.

Stipules: None.

FLOWERS

Flower buds:
- *Size.*—Large.
- *Shape.*—Obtuse and plump.
- *Surface.*—Pubescent.
- *Length.*—5 mm (0.197 inches).
- *Diameter.*—3 mm (0.118 inches).
- *Color.*—Pink-dark pink.

Flowers:
- *Generally.*—Pink-white.

Date of bloom: February 17 to March 1 in Kingsburg, Calif.

Size:
- *Generally.*—Large.

Petals:

- *Color.*—Upper side—pink to light pink. Page 123, Plate 50, I-1. Lower side—light pink to white. Page 123, Plate 50, J-1.

Stamens: 37 to 40.

Pistil: One.

Pollination requirements: Self pollinating.

FRUIT

Maturity when described: Matures about May 15 through May 31, Kingsburg, Calif.

Size: Uniform.
- *Average diameter.*—55 mm (2.165 inches) to 60 mm (2.362 inches).
- *Average diameter transverse in the suture plane.*—57 mm (2.244 inches) to 62 mm (2.440 inches).
- *Average diameter transverse and at right angles to the suture plane.*13 62 mm (2.440 inches) to 64 mm (2.519 inches).

Form:
- *Uniformity.*—Uniform.
- *Symmetry.*—Round, oblong with unequal sides.

Suture:
- *Generally.*—Distinct with shallow groove.
- *Length.*—85 mm (3.346 inches) to 90 mm (3.543 inches).

Ventral surface:
- *Generally.*—Smooth.

Stem cavity:
- *Generally.*—Smooth.
- *Depth.*—20 mm (0.787 inches) in width by 22 mm (0.866 inches) in length by 10 mm (0.393 inches) in depth.
- *Shape.*—Round.

Stem:
- *Caliper—length.*—10 mm (0.393 inches).
- *Caliper—width.*—3 mm (0.118 inches).

Apex:
- *Shape.*—Rounded.

Pistil point: Depressed.

Skin:
- *Thickness.*—Medium.
- *Texture.*—Medium.
- *Tendency to crack.*—None.
- *Pubescence.*—None.
- *Color.*—Uniformly red to dark red with little, if any, medium yellow background. Ground—Page 43, Plate 10, G-6. Blush—Page 37, Plate 7, J-6.

Flesh:
- *Flesh color.* Medium yellow with red streaks around pit cavity. Page 43, Plate 10, G-6.
- *Surface of pit cavity.*—Rough.
- *Color of pit well.*—Same color as the flesh.
- *Amygdalin.*—Scant.
- *Juice production.*—Juicy.
- *Flavor.*—Pleasing.
- *Aroma.*—Distinct.
- *Texture.*—Medium.
- *Fibers.*—Few.
- *Ripening.*—Even.
- *Eating quality.*—Good.

Stone:
- *Attachment.*—Semi-clingstone.
- *Fibers.*—Adhere along the sutures of pit.
- *Size—length.*—37 mm (1.456 inches).
- *Size—width.*—28 mm (1.102 inches).
- *Size—thickness.*—21 mm (0.826 inches).
- *Form—generally.*—Oblong.

*Apex—shape.*—Pointed.
*Color.*—Light tan. Page 43, Plate 10, F-5.
*Base—shape.*—Straight.
*Sides.*—Equal, pitted near base, ridged at apex.
*Ridges.*—Shallow—Slightly rough.
*Size of position of grooves.*—Narrow and shallow near apex.
*Dorsal edge.*—Medium width with shallow groove.
*Tendency to split.*—None.

Use: Fresh fruit.
Keeping quality: good.
Shipping and handling qualities: Good.

Although the new variety of nectarine tree possesses the described characteristics noted above as a result of the growing conditions prevailing near Kingsburg in the central part of the San Joaquin Valley of central California, it is to be understood that variations of the usual magnitude and characteristics incident to changes in growing conditions, fertilization, pruning and pest control are to be expected.

Having thus described and illustrated our new variety of nectarine tree, what we claim as new and desire to be secured by Plant Letters Patent is:

1. A new and distinct variety of nectarine tree substantially as illustrated and described characterized by producing a fruit which is mature approximately May 15 through May 31 in the San Joaquin Valley of central California and which is a semi-clingstone having a bright red coloration, a pleasing flavor and aroma and with noteworthy shipping and handling characteristics.

* * * * *

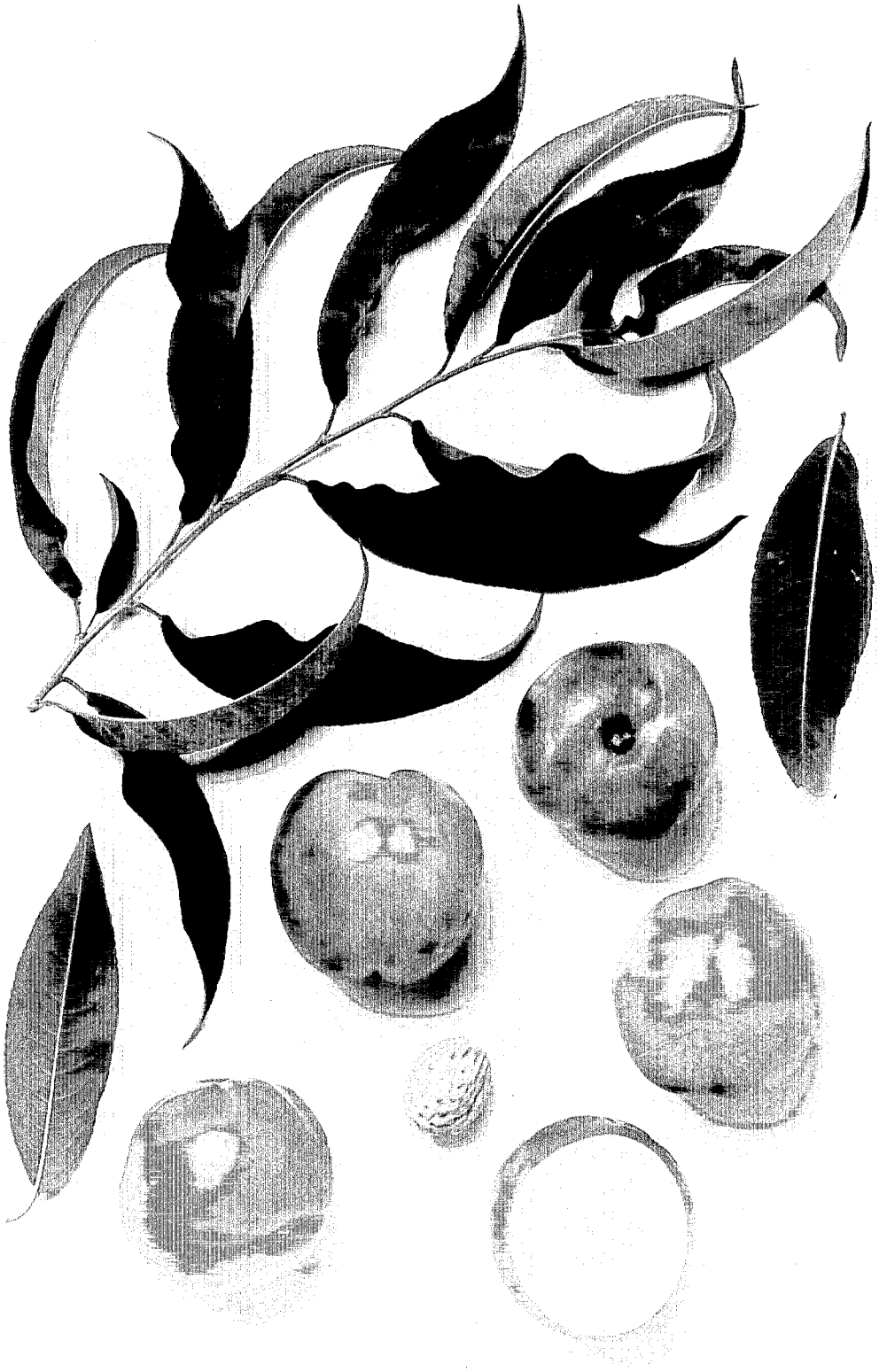

UNITED STATES PATENT AND TRADEMARK OFFICE

CERTIFICATE OF CORRECTION

PATENT NO. : PP 8,255

DATED : June 15, 1993

INVENTOR(S) : James L. Jackson, Lance Jackson

It is certified that error appears in the above-identified patent and that said Letters Patent is hereby corrected as shown below:

Column 3, line 26, delete "(0.0236 inches)." and substitue

---(0.236 inches).---.

Column 4, line 17, between "plane." and "62 mm", delete ---13---.

Column 3, line 32, delete "(6.29 9inches)." and substitue

---(6.299 inches).---.

Signed and Sealed this

Eighth Day of February, 1994

Bruce Lehman

*Attest:*

BRUCE LEHMAN

*Attesting Officer*

*Commissioner of Patents and Trademarks*